US010905779B2

(12) United States Patent
Braithwaite et al.

(10) Patent No.: US 10,905,779 B2
(45) Date of Patent: Feb. 2, 2021

(54) METHODS FOR SCREENING HUMAN BLOOD PRODUCTS COMPRISING PLASMA USING IMMUNOCOMPROMISED RODENT MODELS

(71) Applicants: THE BOARD OF TRUSTEES OF THE LELAND STANFORD JUNIOR UNIVERSITY, Stanford, CA (US); U.S. GOVERNMENT AS REPRESENTED BY THE DEPARTMENT OF VETERANS AFFAIRS, Washington, DC (US); ALKAHEST, INC., San Carlos, CA (US)

(72) Inventors: Steven Braithwaite, San Francisco, CA (US); Saul A. Villeda, Lancaster, CA (US); Anton Wyss-Coray, Palo Alto, CA (US)

(73) Assignees: THE BOARD OF TRUSTEES OF THE LELAND STANFORD JUNIOR UNIVERSITY, Stanford, CA (US); U.S. GOVERNMENT AS REPRESENTED BY THE DEPARTMENT OF VETERANS AFFAIRS, Washington, DC (US); ALKAHEST, INC., San Carlos, CA (US)

( * ) Notice: Subject to any disclaimer, the term of this patent is extended or adjusted under 35 U.S.C. 154(b) by 692 days.

(21) Appl. No.: 15/584,685

(22) Filed: May 2, 2017

(65) Prior Publication Data
US 2017/0232118 A1 Aug. 17, 2017

Related U.S. Application Data

(63) Continuation-in-part of application No. 14/562,401, filed on Dec. 5, 2014.

(60) Provisional application No. 62/331,321, filed on May 3, 2016, provisional application No. 62/069,044, filed on Oct. 27, 2014, provisional application No. 61/913,812, filed on Dec. 9, 2013.

(51) Int. Cl.
A61K 35/16 (2015.01)
A61K 49/00 (2006.01)
A61K 35/12 (2015.01)

(52) U.S. Cl.
CPC .......... *A61K 49/0008* (2013.01); *A61K 35/12* (2013.01); *A61K 35/16* (2013.01)

(58) Field of Classification Search
None
See application file for complete search history.

(56) References Cited

U.S. PATENT DOCUMENTS

| | | | |
|---|---|---|---|
| 4,872,983 A | 10/1989 | Diamantoglou et al. | |
| 5,240,614 A | 8/1993 | Ofsthun et al. | |
| 5,916,202 A | 6/1999 | Haswell | |
| 6,416,487 B1 | 7/2002 | Braverman et al. | |
| 6,419,830 B2 | 7/2002 | Strom et al. | |
| 6,423,024 B1 | 7/2002 | Strom et al. | |
| 6,632,174 B1 | 10/2003 | Breznitz | |
| 6,855,121 B1 | 2/2005 | Chan et al. | |
| 6,946,546 B2 | 9/2005 | Vaughan et al. | |
| 7,196,162 B2 | 3/2007 | Quirk et al. | |
| 7,368,542 B2 | 5/2008 | McIntyre | |
| 7,608,406 B2 | 10/2009 | Valkirs et al. | |
| 7,739,056 B2 | 6/2010 | Landfield et al. | |
| 7,785,601 B2 | 8/2010 | Schaebitz et al. | |
| 7,851,172 B2 | 12/2010 | Lovell et al. | |
| 7,908,090 B2 | 3/2011 | Kim et al. | |
| 8,211,310 B2 | 7/2012 | Young et al. | |
| 8,257,922 B2 | 9/2012 | Liew et al. | |
| 8,272,518 B2 | 9/2012 | Fujita et al. | |
| 8,349,550 B2 | 1/2013 | Brady et al. | |
| 8,772,042 B2 | 7/2014 | Yalkinoglu et al. | |
| 8,778,616 B2 | 7/2014 | Ambati et al. | |
| 8,828,977 B2 | 9/2014 | Zahos et al. | |
| 9,161,968 B2 | 10/2015 | Wyss-Coray et al. | |
| 9,511,094 B2 | 12/2016 | Fraser et al. | |
| 9,770,486 B2 | 9/2017 | Wyss-Coray et al. | |
| 9,782,457 B2 | 10/2017 | Chandler et al. | |
| 2002/0055158 A1 | 5/2002 | Greene et al. | |
| 2002/0143283 A1 | 10/2002 | Braverman et al. | |
| 2002/0151064 A1 | 10/2002 | Rothenberg et al. | |

(Continued)

FOREIGN PATENT DOCUMENTS

EP 0184040 B1 4/1993
EP 2341138 A1 7/2011
(Continued)

OTHER PUBLICATIONS

Villeda et al. (2011) Nature vol. 477: 90-96. (Year: 2011).*
Brehm et al. (2012) Cellular and Molecular Immunology, 9: 225-231 (Year: 2012).*
Nomura et al. (eds.),In.: Humanized Mice, Current Topics in Microbiology and Immunology, 324: pp. 1-24 (Year: 2008).*
Pearson et al. In Humanized Mice, Current Topics in Microbiology and Immunology, 324, pp. 25-51 (Year: 2008).*
Morton et al. (2007) Nature Protocols, vol. 2, No. 2, pp. 247-250. (Year: 2007).*

(Continued)

*Primary Examiner* — Russell G Fiebig
(74) *Attorney, Agent, or Firm* — Casimir Jones, S.C.

(57) ABSTRACT

Methods and compositions are provided for screening candidate compositions for activity with respect to treatment of aging-associated conditions, e.g., cognitive impairment conditions or age-related dementia. Aspects of the methods include administering a human blood product comprising plasma, to an immunocompromised animal, e.g., a mouse or a rat, and measuring the effect of the product on an endpoint, e.g., neurogenesis, locomotor activity, anxiety, spatial memory, and hippocampus-dependent memory.

16 Claims, 6 Drawing Sheets

(56) References Cited

U.S. PATENT DOCUMENTS

| | | |
|---|---|---|
| 2003/0139332 A1 | 7/2003 | Noble et al. |
| 2003/0157687 A1 | 8/2003 | Greene et al. |
| 2004/0120937 A1 | 6/2004 | Wilson |
| 2004/0127445 A1 | 7/2004 | Liew et al. |
| 2004/0141946 A1 | 7/2004 | Schaebitz et al. |
| 2004/0254152 A1 | 12/2004 | Monje et al. |
| 2005/0142101 A1 | 6/2005 | Forssmann et al. |
| 2005/0221348 A1 | 10/2005 | Ray et al. |
| 2005/0244448 A1 | 11/2005 | Chen et al. |
| 2006/0031951 A1 | 2/2006 | Klimanskaya et al. |
| 2006/0094064 A1 | 5/2006 | Ray et al. |
| 2006/0133423 A1 | 6/2006 | Hamada |
| 2006/0198851 A1 | 9/2006 | Basi et al. |
| 2006/0263759 A1 | 11/2006 | Alves-Filho et al. |
| 2007/0037200 A1 | 2/2007 | Ray et al. |
| 2007/0155725 A1 | 7/2007 | Li et al. |
| 2007/0190055 A1 | 8/2007 | Ambati |
| 2008/0026485 A1 | 1/2008 | Hueber et al. |
| 2008/0057590 A1 | 3/2008 | Urdea et al. |
| 2008/0125354 A1 | 5/2008 | Fields et al. |
| 2009/0143394 A1 | 6/2009 | Wyss-Coray et al. |
| 2009/0181008 A1 | 7/2009 | Ray et al. |
| 2009/0209615 A1 | 8/2009 | Lipton et al. |
| 2009/0239241 A1 | 9/2009 | Ray et al. |
| 2010/0015235 A1 | 1/2010 | Watson et al. |
| 2010/0080850 A1 | 4/2010 | Hubbel et al. |
| 2010/0119496 A1 | 5/2010 | Wilkison et al. |
| 2010/0124756 A1 | 5/2010 | Ray et al. |
| 2010/0258496 A1 | 10/2010 | Hidaka et al. |
| 2010/0310609 A1 | 12/2010 | Watson et al. |
| 2010/0324079 A1 | 12/2010 | Ohyagi |
| 2011/0117100 A1 | 5/2011 | Britschgi et al. |
| 2011/0142848 A1 | 6/2011 | Chung et al. |
| 2011/0202284 A1 | 8/2011 | McReynolds et al. |
| 2011/0212854 A1 | 9/2011 | Ray et al. |
| 2011/0243947 A1 | 10/2011 | Doody et al. |
| 2012/0095000 A1 | 4/2012 | Wyss-Coray et al. |
| 2012/0230941 A1 | 9/2012 | Sing et al. |
| 2013/0040844 A1 | 2/2013 | Wyss-Coray et al. |
| 2013/0302322 A1 | 11/2013 | Wong et al. |
| 2014/0011689 A1 | 1/2014 | Sandip et al. |
| 2014/0121438 A1 | 5/2014 | Long et al. |
| 2014/0255424 A1 | 9/2014 | Wyss-Coray et al. |
| 2014/0294724 A1 | 10/2014 | Chain et al. |
| 2015/0031562 A1 | 1/2015 | Kantor et al. |
| 2015/0079045 A1 | 3/2015 | Kong |
| 2015/0157664 A1 | 6/2015 | Wyss-Coray et al. |
| 2016/0208011 A1 | 7/2016 | Wyss-Coray et al. |
| 2017/0081415 A1 | 3/2017 | Wong et al. |
| 2017/0232118 A1 | 8/2017 | Wyss-Coray et al. |

FOREIGN PATENT DOCUMENTS

| | | |
|---|---|---|
| RU | 2428997 C1 | 9/2011 |
| RU | 2470677 C1 | 12/2012 |
| UA | 35656 C2 | 4/2001 |
| WO | WO 1990011287 | 10/1990 |
| WO | WO 1997038314 | 10/1997 |
| WO | WO 1999006098 | 2/1999 |
| WO | WO 2000062836 | 10/2000 |
| WO | WO 2002006480 A2 | 1/2002 |
| WO | WO 2003006006 | 1/2003 |
| WO | WO 2003020403 | 3/2003 |
| WO | WO 2004019043 | 3/2004 |
| WO | WO 2004060425 | 7/2004 |
| WO | WO 2005052592 A2 | 6/2005 |
| WO | WO 2005106492 A2 | 11/2005 |
| WO | WO 2006102170 A2 | 9/2006 |
| WO | WO 2006133423 A1 | 12/2006 |
| WO | WO 2007059135 A2 | 5/2007 |
| WO | WO 2008014314 | 1/2008 |
| WO | WO 2008146018 | 12/2008 |
| WO | WO 2009023814 A2 | 2/2009 |
| WO | WO 2009055729 A1 | 4/2009 |
| WO | WO 2010017443 | 2/2010 |
| WO | WO 2010041617 | 4/2010 |
| WO | WO 2011094535 A2 | 8/2011 |
| WO | WO 2013142135 A1 | 9/2013 |
| WO | WO 2015081166 A1 | 6/2015 |
| WO | WO 2015088915 A1 | 6/2015 |
| WO | WO 2015161112 A1 | 10/2015 |
| WO | WO 2016187217 A2 | 11/2016 |
| WO | WO 2016205004 A2 | 12/2016 |
| WO | WO 2017120461 A1 | 7/2017 |

OTHER PUBLICATIONS

Adachi et al., "Intravascular lymphomatosis: a case report" No Shinkei Geka. Jul. 2001;29(7):659-65. Original in Japanese (English abstract obtained from pubmed).

Adair et al., "Measurement of gelatinase B (MMP-9) in the cerebrospinal fluid of patients with vascular dementia and Alzheimer disease." Stroke. Jun. 2004;35(6):e159-62.

Adkins et al. "Toward a human blood serum proteome: analysis by multidimensional separation coupled with mass spectrometry." Mol Cell Proteomics. Dec. 2002;1(12):947-55.

Anderson et al., "High resolution two-dimensional electrophoresis of human plasma proteins." Proc Natl Acad Sci U S A. Dec. 1977;74(12):5421-5.

Anderson et al., "The human plasma proteome: history, character, and diagnostic prospects." Mol Cell Proteomics. Nov. 2002;1(11):845-67.

Baba et al., "Timp-3 deficiency impairs cognitive function in mice." Lab Invest. Dec. 2009;89(12):1340-7.

Berezovskaya et al., "Colony stimulating factor-1 potentiates neuronal survival in cerebral cortex ischemic lesion." Acta Neuropathol. Nov. 1996;92(5):479-86.

Bhattacharya "Placental umbilical cord whole blood transfusion: a safe and genuine blood substitute for patients of the under-resourced world at emergency." J Am Coll Surg. 2005 . Submitted 34 pages.

Bhattacharya "Study of the utility of placental cord blood in meeting the transfusion needs of beta-thalassaemic patients" Regional Health Forum, 2008. pp. 16-27.

Boissonneault et al., "Powerful beneficial effects of macrophage colony-stimulating factor on beta-amyloid deposition and cognitive impairment in Alzheimer's disease." Brain. Apr. 2009;132(Pt 4):1078-92.

Borlongan et al., "Central nervous system entry of peripherally injected umbilical cord cells is not required for neuroprotection in stroke." Stroke. Oct. 2004;35(10):2385-9.

Bouchard et al. "Aging and brain rejuvenation as systemic events", J. Neurochem. Jan. 2015; 132(1):5-19.

Britschgi et al., "Blood protein signature for the early diagnosis of Alzheimer disease." Arch Neurol. Feb. 2009;66(2):161-5.

Cheung et al., "Serum β-2 microglobulin predicts mortality in people with diabetes." Eur J Endocrinol. May 17, 2013;169(1):1-7.

Conboy et al., "Heterochronic parabiosis for the study of the effects of aging on stem cells and their niches." Cell Cycle. Jun. 15, 2012;11(12):2260-7.

Conboy et al., "Heterochronic parabiosis: historical perspective and methodological considerations for studies of aging and longevity." Aging Cell. Jun. 2013;12(3):525-30.

Conboy et al., "Rejuvenation of aged progenitor cells by exposure to a young systemic environment." Nature. Feb. 17, 2005;433(7027):760-4.

Fedoroff e al., "Role of colony stimulating factor-1 in brain damage caused by ischemic." Neurosci Biobehav Rev. Mar. 1997;21(2):187-91.

Gowing et al., "Macrophage colony stimulating factor (M-CSF) exacerbates ALS disease in a mouse model through altered responses of microglia expressing mutant superoxide dismutase." Exp Neurol. Dec. 2009;220(2):267-75.

Jha, Alok. "Young blood can reverse some effects of ageing, study finds", The Guardian, Oct. 12, 2012, 4 pages.

Katcher "Studies that shed new light on aging." Biochemistry (Mosc). Sep. 2013;78(9):1061-70.

Kwak et al., "Aging, exercise, and extracellular matrix in the heart." J Exerc Rehabil. Jun. 30, 2013;9(3):338-47.

(56) References Cited

OTHER PUBLICATIONS

Lin et al., "Discovery of a cytokine and its receptor by functional screening of the extracellular proteome." Science. May 9, 2008;320(5877):807-11.
Loffredo et al., "Growth differentiation factor 11 is a circulating factor that reverses age-related cardiac hypertrophy." Cell. May 9, 2013;153(4):828-39.
Luo et al. "Colony-stimulating factor 1 receptor (CSF1R) signaling in injured neurons facilitates protection and survival.", J. Exp. Med. (2013) 210(1):157-172.
Lysaght et al., "Beta-2 microglobulin removal during continuous ambulatory peritoneal dialysis (CAPD)." Perit Dial Int. 1989;9(1):29-35.
Malkki, H. "Ageing: Could young blood combat age-related cognitive decline?" Nat. Rev. Neurol. Jun. 2014;10(6):307.
Manzo et al., "Role of chemokines and chemokine receptors in regulating specific leukocyte trafficking in the immune/inflammatory response." Clin Exp Rheumatol. Jul.-Aug. 2003;21(4):501-8.
McLaurin et al., "Microglial pilgrimage to the brain." Nat Med. Dec. 2010;16(12):1380-1.
Middeldorp et al. "A young systemic environment reverses degeneration in a mouse model of Alzheimer's disease", Neuroscience 2012, Presentation Abstract, Oct. 16, 2012, 2 pages.
Mitrasinovic et al., "Microglia overexpressing the macrophage colony-stimulating factor receptor are neuroprotective in a microglial-hippocampal organotypic coculture system." J Neurosci. Apr. 27, 2005;25(17):4442-51.
Mizuno e al., "Interleukin-34 selectively enhances the neuroprotective effects of microglia to attenuate oligomeric amyloid-β neurotoxicity." Am J Pathol. Oct. 2011;179(4):2016-27.
Krementsov "A Martian Stranded on Earth: Alexander Bogdanov, Blood Transfusions, and Proletarian Science" pp. 57-59,85,86, and 88. University of Chicago Press, Chicago, United States, 2011.
Palop et al., "A network dysfunction perspective on neurodegenerative diseases." Nature. Oct. 19, 2006;443(7113):768-73.
Prakasam et al., "Amyloid and Neurodegeneration: Alzheimer's Disease and Retinal Degeneration" Chapter 7, Handbook of Neurochemistry and Molecular Neurobiology, Lajtha ed., 2009, 131-163. (Year: 2009).
Ron-Harel et al. "Age-Dependent Spatial Memory Loss Can Be Partially Restored by Immune Activation", Rejuvenation Resarch (2008), 11(5):903-13.
Royer et al., "A novel antagonist of prostaglandin 02 blocks the locomotion of eosinophils and basophils." Eur J Clin nvesl. Sep. 2008;38(9):663-71.
Schwartz et al. "How Do Immune Cells Support and Shape the Brain in Health, Disease, and Aging?" The Journal of Neuroscience, Nov. 6, 2013, 33(45):17587-96.
Sellebjerg, et al., "Identification of new sensitive biomarkers for the in vivo response to interferon-beta treatment in multiple sclerosis using DNA-array evaluation." Eur J Neurol. Dec. 2009;16(12):1291-8.
Shin et al., "Association of Eotaxin gene family with asthma and serum total IgE." Hum Mol Genet. Jun. 1, 2003;12(11):1279-85.
Skovronsky et al., "Neurodegenerative diseases: new concepts of pathogenesis and their therapeutic implications." Annu Rev Pathol. 2006;1:151-70.
Smith et al., "β2-microglobulin is a systemic pro-aging factor that impairs cognitive function and neurogenesis." Nat Med. Aug. 2015;21(8):932-7.
Strobel et al., "Chicago: The Vampire Principle—Young Blood Rejuvenates Aging Brain?", Alzheimer Research Forum (Nov. 2009), p. 1-3.
Stubbs et al., "Indomethacin causes prostaglandin 0(2)-like and eotaxin-like selective responses in eosinophils and basophils." J Biol Chern. Jul. 19, 2002;277(29):26012-20.
Suzuki et al., "Beta2-microglobulin-selective adsorbent column (Lixelle) for the treatment of dialysis-related amyloidosis." Ther Apher Dial. Feb. 2003;7(1):104-7.

Teixeira, A.L. et al, "Increased serum levels of CCL 11/eotaxin in schizophrenia", Process in Neuro-Psychopharmacology & Biological Psychiatry, vol. 32, No. 3, pp. 710-714, 2008.
Thomson et al. "Young blood for a keener mind", NewScientist (2012), 216(2887):10.
Villeda et al. "The aging systemic milieu negatively regulates neurogenesis and cognitive function", Nature, Aug. 31, 2011, 477(7362):90-4.
Villeda et al. "Young blood reverses age-related cognitive impairments", Neuroscience 2012, Presentation Abstract, Oct. 17, 2012, 2 pages.
Villeda et al. "Young blood reverses age-related impairments in cognitive function and synaptic plasticity in mice", Nat Med. (Jun. 2014), 20(6):659-63.
Villeda et al., "Changes in the systemic milieu modulate neurogenesis during aging" Abstract, 39th Annual Neuroscience Meeting, Chicago, IL, Society for Neuroscience, Oct. 2009, 1-2. (Year: 2009).
Villeda et al., Meeting Date, Past and Future Meetings, 39th Annual Neuroscience Meeting, Society for Neuroscience, 2009, 1. (Year: 2009).
Vincent et al., "Macrophage colony stimulating factor prevents NMDA-induced neuronal death in hippocampal organotypic cultures." J Neurochem. Sep. 2002;82(6):1388-97.
Wang et al., "Expression of colony stimulating factor-1 receptor (CSF-1R) by CNS neurons in mice." J Neurosci Res. Sep. 1, 1999;57(5):616-32.
Wang et al., "Matrix metalloproteinases and their multiple roles in Alzheimer's disease." Biomed Res Int. 2014;2014:908636.
Website document entitled "Plasma Protein Composition" (available at http://www.sigmaaldrich science/metabolomics/enzyme-explorer/learning-center/plasma-blood-proteins/plasma-protein-composition.html). Downloaded from internet Jun. 27, 2017., 3 pages.
Wilson et al., "Beta2-microglobulin as a biomarker in peripheral arterial disease: proteomic profiling and clinical studies." Circulation. Sep. 18, 2007;116(12):1396-403.
Yagihashi A. et al., "Macrophage colony stimulating factor (M-CSF) protects spiral ganglion neurons following auditory nerve injury: morphological and functional evidence." Exp Neurol. Mar. 2005;192(1):167-77.
Yamane et al., "CSF-1 receptor-mediated differentiation of a new type of monocytic cell with B cell-stimulating activity: its selective dependence on IL-34." J Leukoc Biol. Jan. 2014;95(1):19-31.
Ye, et al., "Haptoglobin-alpha subunit as potential serum biomarker in ovarian cancer: identification and characterization using proteomic profiling and mass spectrometry." Clinical Cancer Research (Aug. 2003), 9 (8):2904-11.
SFN "Young blood can reverse some effects of ageing, study finds", Author Unknown, Society for Neuroscience, The Observer, Oct. 24, 2012, 2 pages, Retrieved online: http://gonzoj.wordpress.com/tag/society-for-neuroscience/.
Search Report dated Aug. 2, 2017, for related European application No. 14868769.2, 8 pages.
Search Report of related PCT/US2011/022916, dated Oct. 31, 2011, 11 pages.
Search Report of related PCT/US2014/068897, dated Feb. 27, 2015, 11 pages.
Search Report of related PCT/US2016/032907, dated Dec. 1, 2016, 24 pages.
Search Report of related PCT/US2016/036032, dated Feb. 21, 2017, 13 pages.
Search Report of related PCT/US2017/012521, dated Feb. 2, 2017, 12 pages.
Examiner Report of 2016265948, dated May 11, 2018, 6 pages.
Examiner Report of 738184, dated Apr. 6, 2018, 4 pages.
Allodi "modeling motor neuron resilience in ALS using stem cells" accessed from biorxiv (Year: 2018), 28 pages.
Ameer et al., "A novel immunoadsorption device for removing beta2-microglobulin from whole blood." Kidney Int. Apr. 2001;59(4):1544-50.
Archibald et al., "The retina in Parkinson's disease." Brain. May 2009;132(Pt 5):1128-45.

(56) References Cited

OTHER PUBLICATIONS

Brew et al., "The tissue inhibitors of metalloproteinases: An ancient family with structural and functional diversity," Biochimica et Biophysica Acta (2010) 1803: 55-71).
Cairo CW et al., Drug-Receptor Interactions, Principles of Pharmacology, (2nd ed.), Chapter 1, pp. 3-18 (2008)).
GHR "Parkinson's disease" accessed from ghr.nlm.nih.gov on Mar. 15, 2019 (Year: 2019), 10 pages.
Giorgetti et al., "beta2-Microglobulin is potentially neurotoxic, but the blood brain barrier is likely to protect the brain from its toxicity." Nephrol Dial Transplant. Apr. 2009;24(4):1176-81.
Gomez, et al., "Tissue inhibitors of metalloproteinases: structure, regulation and biological functions," European Journal of Cell Biology (1997) 74: 111-22).
Kassiri, et al., "Tissue inhibitor of metalloproteinases (TIMPs) in heart failure," Heart Failure Reviews (2012) 17: 693-706).
Komosinkska-Vassev, et al., "Age-and gender-dependent changes in connective tissue remodeling: physiological differences in circulating MMP-3, MMP-10, TIMP-1, and TIMP-2 levels," Gerontology (2011) 57: 44-52).
Lee, et al., "Effects of aging on blood brain barrier and matrix metalloproteases following controlled cortical impact in mice," Experimental Neurology (2012) 234: 50-61).
Longo "Alzheimer's Prevention, Treatment and Research-A Q&A" Stanford Health Now, 2016, 1-2.
Perez-Martinez et al. "Tissue inhibitor of metalloproteinase-2 promotes neuronal differentiation by acting as an anti-mitogenic signal." J Neurosci. May 18, 2005;25(20):4917-29.
Martino et al., "Circulating MicroRNAs Are Not Eliminated by Hemodialysis" (2012) Circulating MicroRNAs Are Not Eliminated by Hemodialysis. PLOS ONE 7(6): e38269.
Mayer et al., "Identification of receptor binding and activation determinants in the N-terminal and N-loop regions of the CC chemokine eotaxin."J Biol Chem. Apr. 27, 2001;276(17):13911-6.
Moore et al., "An Alternate Perspective on the Roles of TIMPs and MMPs in Pathology," The American Journal of Pathology (2012) 180: 12-16).
Murphy, "Tissue inhibitors of metalloproteinases," Genome Biology (2011) 12).
Niezgoda et al., "The effect of cladribine treatment on beta-2 microglobin in the cerebrospinal fluid and serum of patients with multiple sclerosis" Neurol Neurochir Pol. Mar.-Apr. 2000;34(2):281-7. (Abstract).
Politis et al., "Parkinson's disease symptoms: the patient's perspective." Mov Disord. Aug. 15, 2010;25(11):1646-51.
Reitz, "Toward precision medicine in Alzheimer's disease." Ann Transl Med. Mar. 2016;4(6):107.
Shen et al., "CCR3 monoclonal antibody inhibits airway eosinophilic inflammation and mucus overproduction in a mouse model of asthma." Acta Pharmacol Sin. Dec. 2006;27(12):1594-9.
Stetler-Sstevenson et al., "TIMP-2: an endogenous inhibitor of angiogenesis," Trends in Molecular Medicine (2005) 11: 97-103).
Stetler-Stevenson, "Tissue Inhibitors of Metalloproteinases in Cell Signaling," Science Signaling (2008) 1).
Takeda et al., "CCR3 is a target for age-related macular degeneration diagnosis and therapy." Nature. Jul. 9, 2009;460(7252):225-30.
Visse et al. "Matrix Metalloproteinases and Tissue Inhibitors of Metalloproteinases," Circulation Research (2003) 92: 827-39).
Wang et al., "Upregulation of CCR3 by age-related stresses promotes choroidal endothelial cell migration via VEGF-dependent and -independent signaling." Invest Ophthalmol Vis Sci. Oct. 21, 2011;52(11):8271-7.
Wikipedia A "Huntingtin" accessed on Mar. 15, 2019 (excerpt) (Year: 2019).
Wikipedia B "Huntington's disease (Genetics)" accessed Mar. 15, 2019 (excerpt) (Year: 2019).
Xu, et al., "Matrix Metalloproteinase Inhibitors: A review on Bioanalytical Methods, Pharmacokinetics and Metabolism," Current Drug Metabolism (2011) 12: 395-410).
Zheng et al., "Agonist-selective signaling of G protein-coupled receptor: mechanisms and implications." IUBMB Life. Feb. 2010;62(2):112-9.
Examiner Report of 720949, dated Jan. 18, 2019, 5 pages.

* cited by examiner

Figure 3
Fig. 3A
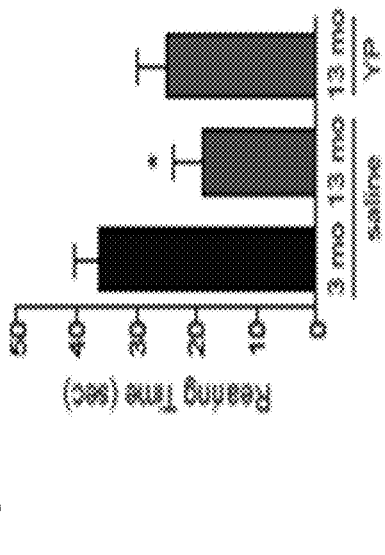
Open Field
Fig. 3B
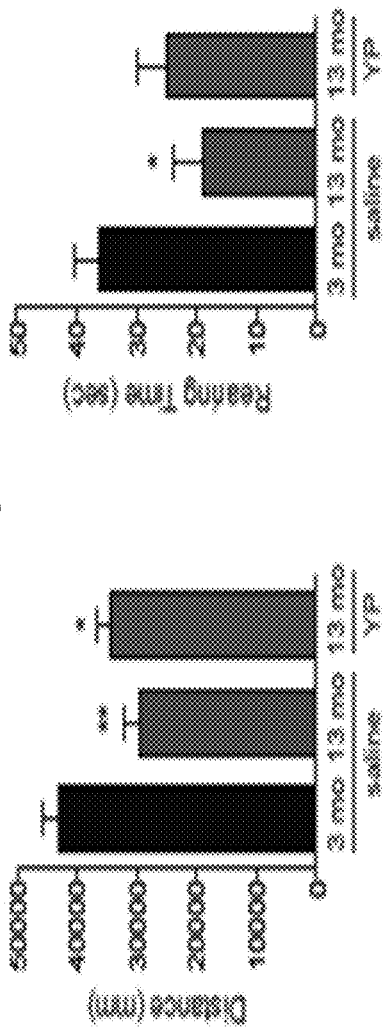
Fig. 3C
Fig. 3D
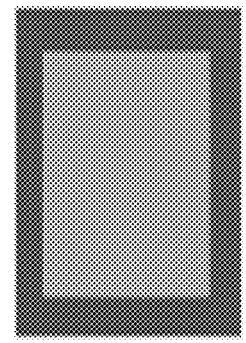
Barnes maze
Fig. 3E
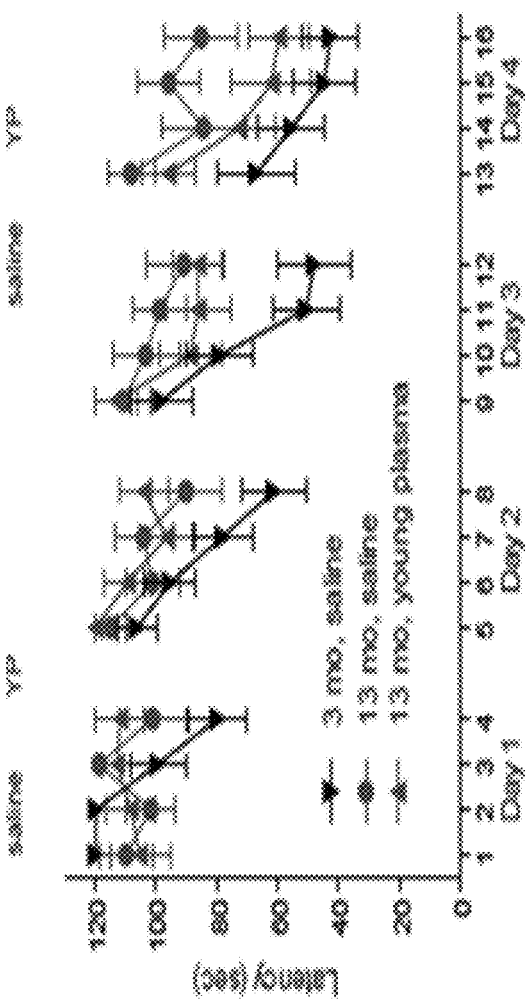

METHODS FOR SCREENING HUMAN BLOOD PRODUCTS COMPRISING PLASMA USING IMMUNOCOMPROMISED RODENT MODELS

CROSS-REFERENCE TO RELATED APPLICATIONS

This application is a continuation-in-part application of U.S. patent application Ser. No. 14/562,401, filed Dec. 5, 2014, which application, pursuant to 35 U.S.C. § 119 (e), claims priority to the filing date of the U.S. Provisional Patent Application Ser. No. 62/069,044, filed Oct. 27, 2014, and U.S. Provisional Patent Application Ser. No. 61/913,812, filed Dec. 9, 2013; the disclosures of which applications are herein incorporated by reference.

Pursuant to 35 U.S.C. § 119 (e), this application also claims priority to the filing date of the United States Provisional Patent Application Ser. No. 62/331,321, filed May 3, 2016; the disclosure of which is herein incorporated by reference.

STATEMENT REGARDING FEDERALLY-SPONSORED RESEARCH

This invention was made with Government support under contract AG045034 awarded by the National Institutes of Health. The Government has certain rights in the invention.

INTRODUCTION

Aging in an organism is accompanied by an accumulation of changes over time. In the nervous system, aging is accompanied by structural and neurophysiological changes that drive cognitive decline and susceptibility to degenerative disorders in healthy individuals. (Heeden, T. & Gabrieli, J. D., Insights into the ageing mind: a view from cognitive neuroscience. Nat. Rev. Neurosci. 5(2), 87-96 (2004); Raz, N. et al. Neuroanatomical correlates of cognitive aging: evidence from structural magnetic resonance imaging. Neuropsychology 12(1), 95-114 (1998); Mattson, M. P. & Magnus, T., Ageing and neuronal vulnerability. Nat. Rev. Neurosci. 7(4), 278-294 (2006); Rapp, P. R. & Heindel, W. C., Memory systems in normal and pathological aging. Curr. Opin. Neural. 7(4), 294-298 (1994)). Included in these changes are synapse loss and the loss of neuronal function that results. Thus, although significant neuronal death is typically not observed during the natural aging process, neurons in the aging brain are vulnerable to sub-lethal age-related alterations in structure, synaptic integrity, and molecular processing at the synapse, all of which impair cognitive function.

In addition to the normal synapse loss during natural aging, synapse loss is an early pathological event common to many neurodegenerative conditions, and is the best correlate to the neuronal and cognitive impairment associated with these conditions. Indeed, aging remains the single most dominant risk factor for dementia-related neurodegenerative diseases such as Alzheimer's disease (AD) (Bishop, N. A., Lu, T., & Yankner, B. A., Neural mechanisms of ageing and cognitive decline. Nature 464(7288), 529-535 (2010); Heeden, T. & Gabrieli, J. D., Insights into the ageing mind: a view from cognitive neuroscience. Nat. Rev. Neurosci. 5(2), 87-96 (2004); Mattson, M. P. & Magnus, T., Ageing and neuronal vulnerability. Nat. Rev. Neurosci. 7(4), 278-294 (2006)).

As human lifespan increases, a greater fraction of the population suffers from aging-associated cognitive impairments, making it crucial to elucidate means by which to maintain cognitive integrity by protecting against, or even counteracting, the effects of aging (Hebert, L. E. et al. Alzheimer disease in the US population: prevalence estimates using the 2000 census. Arch. Neural. 60(8), 1119-1122 (2003); Bishop, N. A., et al., Neural mechanisms of ageing and cognitive decline. Nature 464(7288), 529-535 (2010)).

Assessing cognitive behaviors and their modulation by therapeutics in animal models, particularly mouse and other rodent models is important for the development of therapeutics for a range of neurodegenerative disorders and other indications associated with cognitive decline. Testing of certain potential therapeutics in animals requires the consideration of their off target effects that could confound behavioral outcomes, which highlights the importance of identifying the appropriate animal model in which to test a therapeutic. Although the negative regulation of the aging systemic milieu has been described using mouse parabiosis, this model involves the effects of mouse systemic factors (e.g. from an aged mouse) upon the cognitive and molecular endpoints in the same species but of a different age (e.g. the effect upon a young mouse) (Saul. A. Villeda et al., *The ageing systemic milieu negatively regulates neurogenesis and cognitive function.* 477 Nature 90 (2011)).

The testing of human derived reagents and proteins that would be attractive candidates for treatment of aging-associate cognitive impairment in mice is confounded by the fact that heterologous species would generate immune responses. It is possible that this problem may be circumvented by the use of immunocompromised models; however the characterization of: their tolerance to human blood products comprising plasma; and their cognitive functions in aging has not been adequately explored. Thus, there remains a need for an animal model which will tolerate exogenous human blood plasma comprising products while demonstrating those products' effectiveness. Such a method of screening these products will accelerate discovery of human-specific products.

SUMMARY

Methods and compositions are provided for screening candidate compositions for activity with respect to treatment of aging associated conditions e.g., cognitive impairment conditions or age-related dementia. Aspects of the methods include administering a human blood product comprising plasma, to an immunocompromised animal, e.g. a mouse or a rat and measuring the effect of the product on an endpoint, e.g. neurogenesis, locomotor activity, anxiety, spatial memory, and hippocampus-dependent memory.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A shows the setup of the Open Field test. Mice were placed in a 50 cm×50 cm Open Field arena for 10 minutes, and total distance travelled and rearing behavior were measured. FIG. 2B shows that old mice treated with saline travelled less distance in the arena than young mice and displayed less rearing. FIG. 2C shows that young plasma (YP) improved distance travelled and rearing in old mice, which were not different from young mice (n=18, 8, 9, *p<0.05 by one-way ANOVA). FIG. 2D shows the setup of the Y-Maze test. Mice were allowed to explore two arms of a Y-maze (start+familiar) for 5 minutes. One hour later, mice were allowed to explore all three arms, and total time and number of entries in the arms were recorded. FIG. 2E illustrates that young mice and YP-treated old mice spent significantly more time in the novel arm, while FIG. 2F shows that young mice and YP-treated old mice entered the novel arm more than the familiar arm (n=18, 8, 7, *p<0.05, ***p<0.001 by paired student's t-test).

FIG. 3A depicts the Open Field arena setup. Mice were placed in a 50 cm×50 cm Open Field arena for 15 minutes, and total distance travelled and rearing behavior were measured. FIG. 3B shows that old mice treated with saline travelled less distance in the arena than young mice and showed less rearing. FIG. 3C shows that young plasma (YP)-treated old mice were not different from young mice in rearing time (n=20, 16, 17, *p<0.05, P<0.01 by one-way ANOVA compared to young controls). FIG. 3D depicts the Barnes maze setup. Mice were trained on four consecutive days in the Barnes maze and given a maximum of 120 second to find the escape hole. The escape hole remained the same for four trials on a training day, but changed between training days. FIG. 3E depicts latency recorded to the escape hole for each cohort on four separate training days.

DETAILED DESCRIPTION

Figures 1, 1A, 1B:
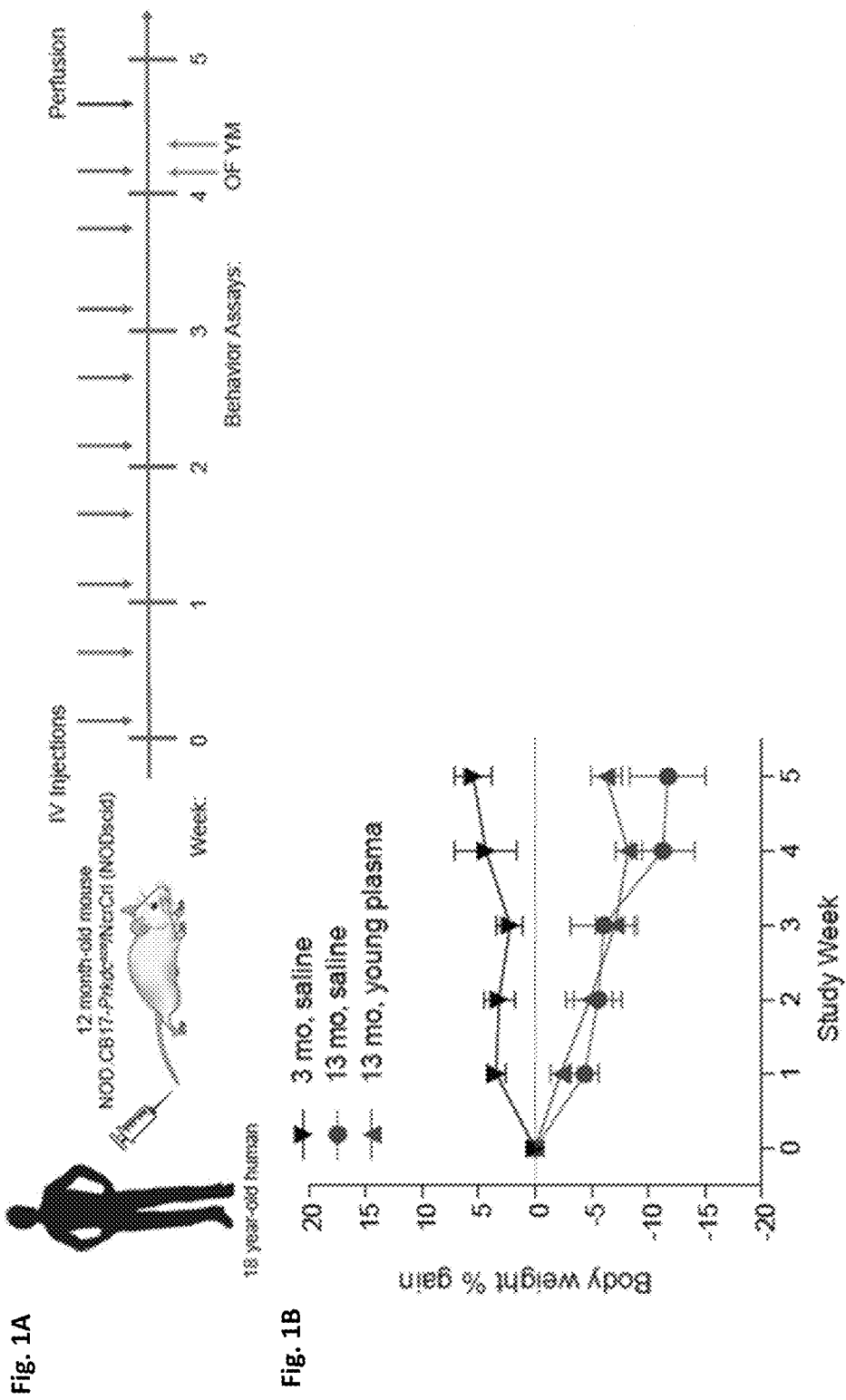
FIG. 1. Young human plasma can be safely administered in aged NODscid mice.
FIG. 1A illustrates that young (2 month old) and old (12 month old) NODscid mice were safely injected with 150 µL of saline control or plasma from young (18-year-old) human donors, twice weekly, for 5 weeks. These mice were tested for locomotor activity and cognition in the Open Field and Y-Maze tests, respectively, in Week 5.
FIG. 1B shows that body weights of the mice were measured once per week for young control-treated, old control-treated, and old plasma-treated groups until study completion (n=18, 13, 13, respectively). No adverse effects of young human plasma administration on body weight was observed.
Figure 2:
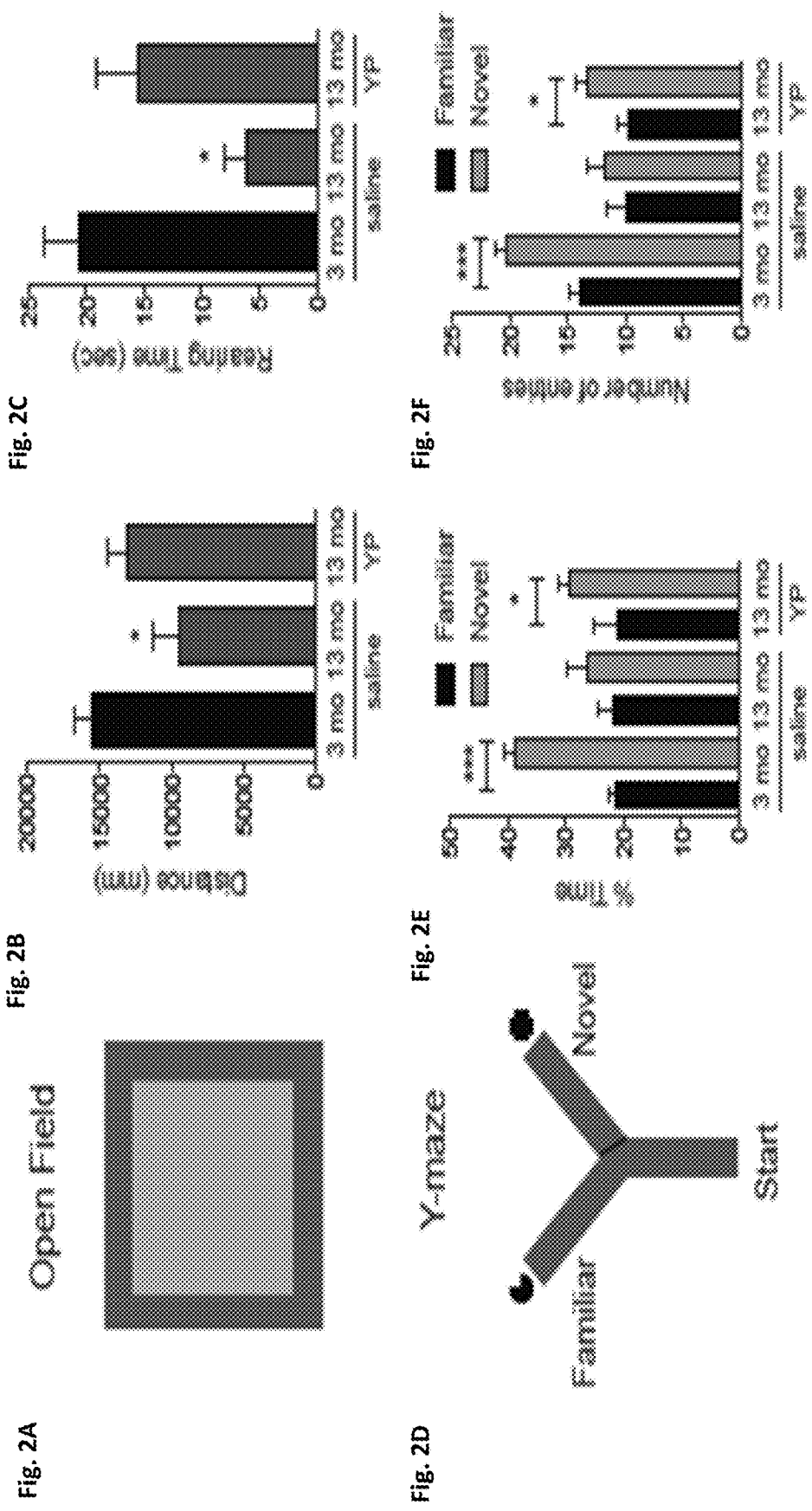
FIG. 2. Young human plasma in aged NODscid mice improves locomotor activity and cognition.
Figures 3, 3F:
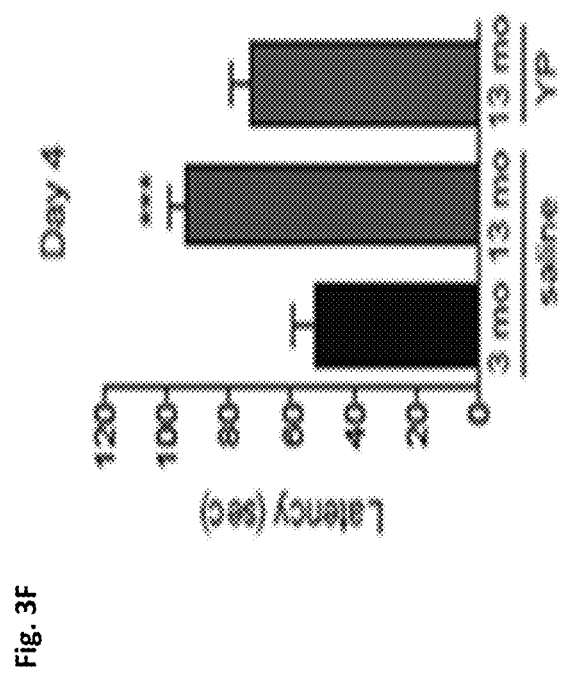
FIG. 3. Young human plasma in aged NSG mice improves locomotor activity and cognition.
FIG. 3F shows that old mice took significantly longer to find the escape hole than young mice (n=15, 11, 12, *p<0.001 by one-way ANOVA).
Figures 4, 4A, 4B:
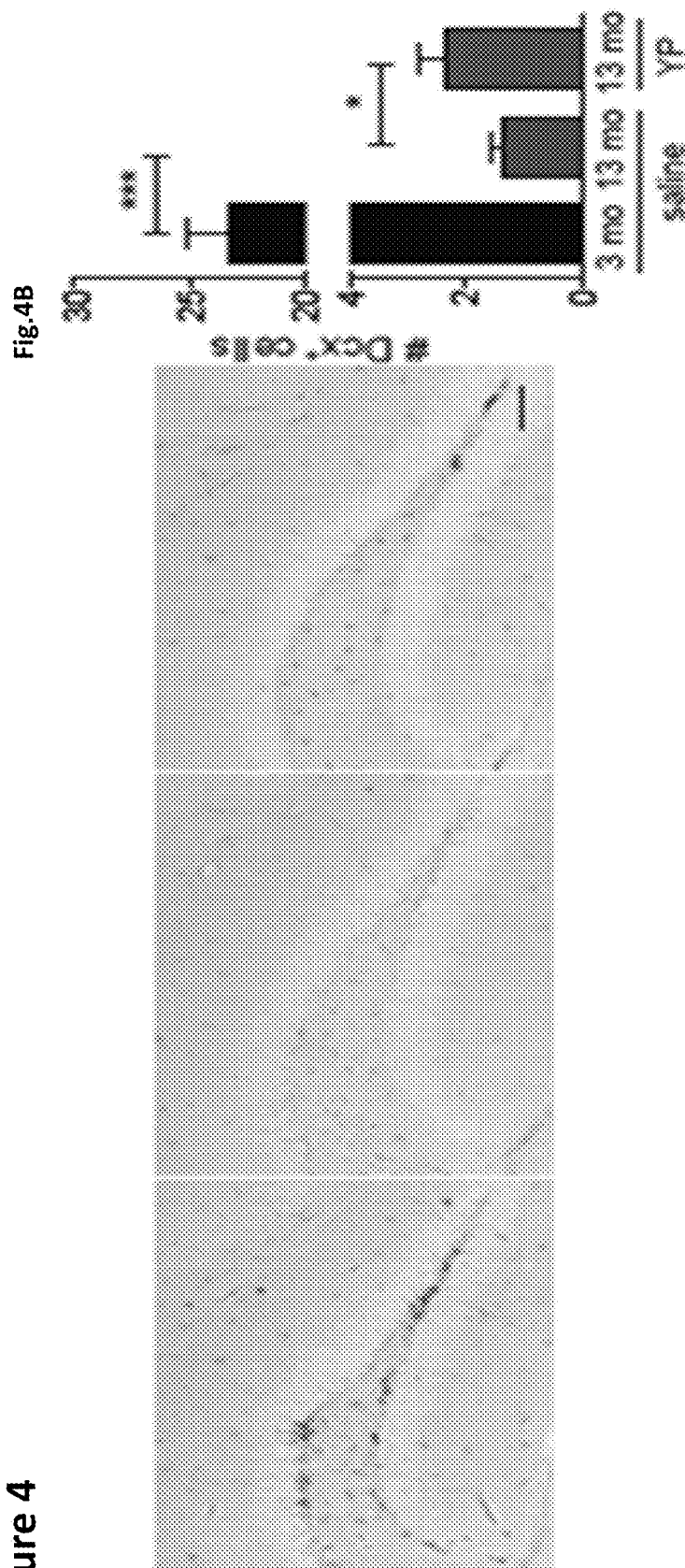
FIG. 4. Young human plasma in aged NSG mice increases neurogenesis.
FIG. 4A presents representative images of hippocampal sections from 3 month-old mice treated with saline (left), 13 month-old mice treated with saline (center), or 13 month-old mice treated with young human plasma (YP) (right).
FIG. 4B shows the quantification of Doublecortin (Dcx)-positive cells. A significant decrease in old NSG mice compared to young NSG mice was observed. Old NSG mice treated with young human plasma show increased number of Dcx-positive cells in the dentate gyrus (n=2, 18, 17, *p<0.05, ***p<0.001 by one-way ANOVA). The scale bar indicates 150 μm.
Figures 5, 5A, 5B:
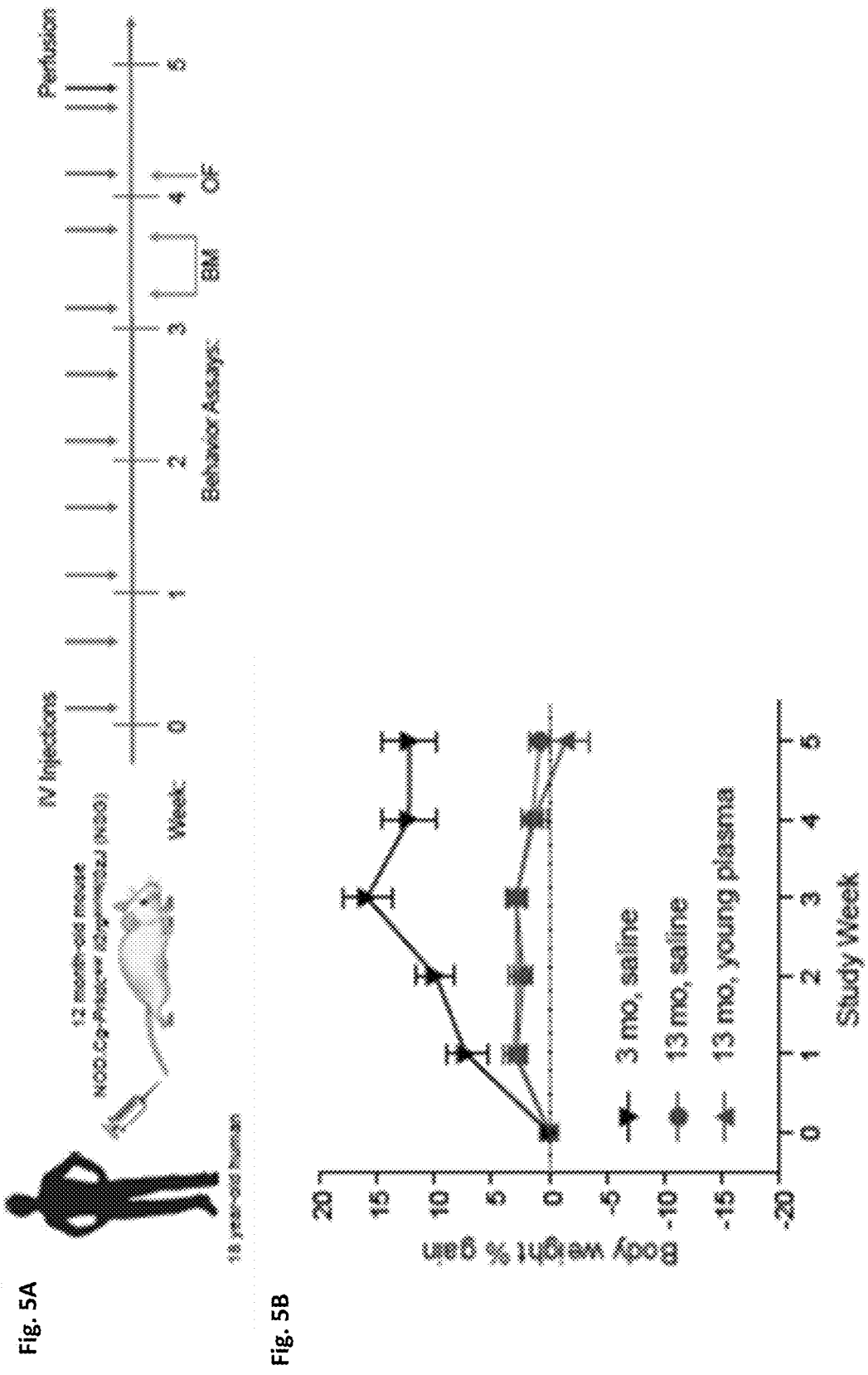
FIG. 5. Young human plasma in aged NSG mice does not adversely affect body weight.
FIG. 5A illustrates that young (2 month-old) and old (12 month-old) NSG mice were injected with 150 μL of saline control or plasma from young human donors (18 years-old) twice weekly, for five weeks.
FIG. 5B shows that body weights were measured once per week until study completion (n=20, 19, 18). No adverse effect of young human plasma administration on body weight was observed.

Methods are provided for screening candidate compositions for activity with respect to treatment of aging associated conditions, e.g., cognitive impairment conditions, age-related dementia or age related decline of physiological function of peripheral organ(s). Aspects of the methods include administering a human blood product comprising plasma to an immunocompromised rodent, such as a mouse, and measuring the effect of the product on an endpoint. The endpoint may be comprised of one or more of the following: neurogenesis, locomotor activity, anxiety, spatial memory, hippocampus-dependent memory, and body weight. These endpoints are described merely as examples, and one of ordinary skill in the art would recognize that there are additional endpoints which can be measured.

Before the present methods and compositions are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

Further, the dates of publication provided may be different from the actual publication dates which may need to be independently confirmed.

Methods

As summarized above, aspects of the invention include methods for treating a subject for aging-associated conditions. By aging-associated condition is meant a condition, e.g., a disease condition or other undesirable condition, which accompanies aging of an organism. The aging associated condition may manifest in a number of different ways, e.g., as aging associated damage to central or peripheral organs of the body, such as but not limited to: cell injury, tissue damage, organ dysfunction, aging-associated lifespan shortening and carcinogenesis, where specific organs and tissues of interest include, but are not limited to skin, neuron, muscle, pancreas, brain, kidney, lung, stomach, intestine, spleen, heart, adipose tissue, testes, ovary, uterus, liver and bone. In some instances, treatment of a subject in accordance with the methods results in a change in a central organ, e.g., a central nervous system organ, such as the brain, spinal cord, etc., where the change may manifest in a number of different ways, e.g., as described in greater detail below, including but not limited to molecular, structural and/or functional. In some instances, treatment of a subject in accordance with the methods results in a change in a peripheral organ, such as liver, muscle, heart, blood, etc., where the change may manifest in a number of different ways, e.g., as described in greater detail below.

In some embodiments, the aging-associated condition that is treated is an aging-associated impairment in cognitive ability in an individual. By cognitive ability, or "cognition", it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated cognitive impairment," it is meant an impairment in cognitive ability that is typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington disease, amyotrophic lateral sclerosis, multiple sclerosis, glaucoma, myotonic dystrophy, vascular dementia, and the like.

By "treatment", "treating" and the like it is generally meant obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may results in a variety of different physical manifestations, e.g., modulation in gene expression, rejuvenation of tissue or organs, etc. The therapeutic agent may be administered before, during or after the onset of disease or injury. The treatment of ongoing disease, where the treatment stabilizes or reduces the undesirable clinical symptoms of the patient, is of particular interest. Such treatment may be performed prior to complete loss of function in the affected tissues. The subject therapy may be administered during the symptomatic stage of the disease, and in some cases after the symptomatic stage of the disease.

In some instances where the aging-associated condition is aging-associated cognitive decline, treatment by methods of the present disclosure slows, or reduces, the progression of aging-associated cognitive decline. In other words, cognitive abilities in the individual decline more slowly following treatment by the disclosed methods than prior to or in the absence of treatment by the disclosed methods. In some instances, treatment by methods of the present disclosure stabilizes the cognitive abilities of an individual. For example, the progression of cognitive decline in an individual suffering from agingassociated cognitive decline is halted following treatment by the disclosed methods. As another example, cognitive decline in an individual e.g., an individual 40 years old or older, that is projected to suffer from aging-associated cognitive decline, is prevented following treatment by the disclosed methods. In other words, no (further) cognitive impairment is observed. In some instances, treatment by methods of the present disclosure reduces, or reverses, cognitive impairment, e.g., as observed by improving cognitive abilities in an individual suffering from aging-associated cognitive decline. In other words, the cognitive abilities of the individual suffering from aging-associated cognitive decline following treatment by the disclosed methods are better than prior to treatment by the disclosed methods, i.e., they improve upon treatment. In some instances, treatment by methods of the present disclosure abrogates cognitive impairment. In other words, the cognitive abilities of the individual suffering from aging-associated cognitive decline are restored, e.g., to their level when the individual was about 40 years old or less, following treatment by the disclosed methods, e.g., as evidenced by improved cognitive abilities in an individual suffering from aging-associated cognitive decline.

In practicing the subject methods, a young plasma-comprising blood product is administered to an individual in need thereof, e.g., an individual suffering or at risk of suffering from an aging associated condition, e.g., aging-associated cognitive impairment or age-related dementia. As such, methods according to embodiments of the invention including administering a plasma-comprising product from a young individual (the "donor individual", or "donor") to an individual at least at risk of suffering from an aging-associated cognitive impairment, i.e., an individual suffering or at risk of suffering from an aging associated cognitive impairment (the "recipient individual" or "recipient"). By a "plasma comprising blood product," or "blood product comprising plasma components" it is meant any product derived from blood that comprises plasma. The term "plasma" is used in its conventional sense to refer to the straw colored/pale-yellow liquid component of blood composed of about 92% water, 7% proteins such as albumin, gamma globulin, anti-hemophilic factor, and other clotting factors, and 1% mineral salts, sugars, fats, hormones and vitamins. Non-limiting examples of plasma comprising blood products suitable for use in the subject methods include whole blood treated with anti-coagulant (e.g., EDTA, citrate, oxalate, heparin, etc.), blood products produced by filtering whole blood to remove white blood cells ("leukoreduction"), and blood product consisting essentially of purified plasma. In some instances, young plasma product that is employed is a non-whole blood plasma product, by which is meant that the product is not whole blood, such that it lacks one or more components found in whole blood, such as erythrocytes, leukocytes, etc., at least to the extent that these components are present in whole blood. In some instances, the young plasma product is substantially, if not completely, acellular, where in such instances the cellular content may be 5% or less, such as 1% or less, including 0.5% or less.

The terms "individual," "subject," "host," "patient," and animal are used interchangeably herein and refer to any mammalian subject for whom diagnosis, treatment, or therapy is desired, particularly humans. Typically, the donor and recipient will be of the same species. Mammalian species that may be treated with the present methods include rodents, canines and felines; equines; bovines; ovines; etc. and primates, particularly humans. The subject methods, compositions, and reagents may also be applied to animal models, particularly small mammals, e.g., murine, lagomorpha, etc., for example, in experimental investigations.

The discussion below will focus on the application of the subject methods, compositions, reagents, devices and kits to humans, but it will be understood by the ordinarily skilled artisan that such descriptions can be readily modified to other mammals of interest based on the knowledge in the art.

By a "young individual" it is meant an individual that is 40 years old or younger, e.g., 35 years old or younger, including 30 years old or younger, e.g., 25 years old or younger. In some instances, the individual that serves as the source of the young plasma-comprising blood product is one that is 10 years old or younger, e.g., 5 years old or younger, including 1 year old or younger. In some instances, the subject is a newborn and the source of the plasma product is the umbilical cord, where the plasma product is harvested from the umbilical cord of the new born. As such, "young individual" may refer to a subject that is between the ages of 0 and 40, e.g., 0, 1, 5, 10, 15, 20, 25, 30, 35, or 40 years old. In other instances, "young" and "young individual" may refer to a biological (as opposed to chronological) age such as an individual who has not exhibited the levels of inflammatory cytokines in the plasma exhibited in comparatively older individuals. Conversely, these "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 1.5-fold. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest.

By "an individual suffering from or at risk of suffering from an aging-associated cognitive impairment" it is meant to include an individual that is about 50 years old or older, e.g., 60 years old or older, 70 years old or older, 80 years old or older, and usually no older than 100 years old, such as 90 years old, i.e., between the ages of about 50 and 100, e.g., 50, 55, 60, 65, 70, 75, 80, 85 or about 90 years old, and suffers from an aging associated condition, e.g., cognitive impairment, associated with the natural aging process, e.g., M.C.I.; an individual that is about 50 years old or older, e.g., 60 years old or older, 70 years old or older, 80 years old or older, 90 years old or older, and usually no older than 100 years old, i.e., between the ages of about 50 and 100, e.g., 50, 55, 60, 65, 70, 75, 80, 85, 90, 95 or about 100 years old, that has not yet begun to show symptoms of an aging associated condition, e.g., cognitive impairment; an individual of any age that is suffering from a cognitive impairment due to an aging-associated disease, e.g., Alzheimer's disease, Parkinson's disease, frontotemporal dementia, Huntington disease, amyotrophic lateral sclerosis, multiple sclerosis, glaucoma, myotonic dystrophy, dementia, and the like, and an individual of any age that has been diagnosed with an aging-associated disease that is typically accompanied by cognitive impairment, e.g., Alzheimer's disease, Parkinson's disease, frontotemporal dementia, progressive supranuclear palsy, Huntington disease, amyotrophic lateral sclerosis, spinal muscular atrophy, multiple sclerosis, multisystem atrophy, glaucoma, ataxias, myotonic dystrophy, dementia, and the like, where the individual has not yet begun to show symptoms of cognitive impairment.

In some instances, the donor of the blood product (i.e., the young individual) is different from the recipient (i.e., the individual suffering from or at risk of suffering from an aging associated-cognitive impairment). In other words, the blood product is allogeneic to the recipient. In some such instances, the blood product to be administered is selected based upon the blood type of the donor and the blood type of the recipient. By blood type, it is meant the presence or absence of A and B antigens and Rh antigen on the donor and recipient's red blood cells. For example, as is well understood in the art, an individual may have neither A or B antigens on his red blood cells (and hence will have antibodies specific for both A and B antigens in his plasma), in which case the individual is "type O". The individual may have A antigen and not B antigen on his red blood cells (and hence will have antibodies specific for B antigen but not A antigen in his plasma), in which case the individual is "type A." The individual may have B antigen and not A antigen on his red blood cells (and hence antibodies specific for A antigen but not B antigen in his plasma), in which case the individual is "type B." The individual may have both A and B antigens on his red blood cells (and hence no antibodies for either A or B antigen in his plasma), in which case the individual is "type AB." As well known in the art, safe transfusion of donor blood to a recipient can occur if the donor is type O and the recipient is any type; if the donor is type A and the recipient is type A or type AB; if the donor is type B and the recipient is type B or type AB; or if the donor is type AB and the recipient is type AB. Additionally, as is known in the art, the Rh antigen may or may not be present, i.e., the individual is Rh-positive or Rh negative, respectively. As is well known in the art, safe transfusion of donor blood to a recipient can occur if the donor is type Rh+ or Rh+ and the recipient is type Rh\ or if the donor is type Rh− and the recipient is type Rh−. In other such instances, e.g., when the blood product is a fractionated product that comprises no cells displaying the A/B or Rh antigens, for example, a blood product that consists essentially of plasma, the blood product from a donor of any blood type may be administered to the recipient.

In other instances, the donor and the recipient are the same individual, i.e., the blood is drawn from an individual, and the blood product that is prepared from that blood draw is transferred back (restored) into the same individual, e.g., 10 years or more later, e.g., 10, 20, 30, 40, 50, 60, 70, 80, or 90 years later. In other words, the blood product is autologous to the recipient. For example, the blood may have been harvested from the individual when the individual was about 40 years old or younger, e.g., between the ages of 10 and 40, e.g., 10, 15, 20, 25, 30, 35, or 40 years old; and is transfused back into the individual when the individual is about 50 years old or older, e.g., between the ages of 50 and 90, e.g., 50, 55, 60, 65, 70, 75, 80, 85, 90, 95 or about 100 years old. Thus, in particular embodiments of the invention, blood is harvested from an individual, preserved, and transferred back into that individual at an older age.

As indicated above, the blood product suitable for use in the subject methods is a plasma-comprising blood product prepared from blood drawn from a young individual. The blood may be drawn manually, with automated equipment, or with some combination thereof. Any convenient volume may be drawn that does not endanger the life of the donor. In some instances, a volume of 200-600 milliliters of plasma-comprising blood product is drawn, for example 300-550 ml, or 450-500 ml. The drawn blood may be treated with an agent that prevents coagulation, i.e., an anti-coagulant, e.g., EDTA, citrate, oxalate, heparin, etc. For example, anti-coagulant may be added to the blood as it is drawn. As another example, the receptacle into which the blood is collected may comprise anti-coagulant. Other agents, e.g., buffers, preservatives, e.g., phosphate, dextrose, adenine, glycerine, glucose, raffinose, etc., agents that kill viruses, e.g., solvent detergent, etc., may also be added to the blood.

An embodiment of the methods described herein includes the administration of plasma fractions to an animal. Fractionation is the process by which certain protein subsets are separated from plasma. Fractionation technology is known in the art and relies on steps developed by Cohn et al. during the 1940s. (E. Cohn, Preparation and properties of serum and plasma proteins. IV. A system for the separation into fractions of the protein and lipoprotein components of biological tissues and fluids. 68 J Am Chem Soc 459 (1946), herein incorporated by reference). Several steps are involved in this process, each step involving specific ethanol concentrations as well as pH, temperature, and osmolality shifts which result in selective protein precipitation. Precipitates are also separated via centrifugation or precipitation. The original "Cohn fractionation process" involved separation of proteins through precipitates into five fractions, designated fraction I, fraction II+III, fraction IV-1, fraction IV-4 and fraction V. Albumin was the originally identified endpoint (fraction V) product of this process, but one of skill in the art would recognize that each fraction (or effluent from a prior separation step) contains or potentially contains therapeutically-useful protein fractions. (See Thierry Burnouf, Modern Plasma Fractionation, 21(2) Transfusion Medicine Reviews 101 (2007); Adil Denizli, Plasma fractionation: conventional and chromatographic methods for albumin purification, 4 J. Biol. & Chem. 315, (2011); and T. Brodniewicz-Proba, Human Plasma Fractionation and the Impact of New Technologies on the Use and Quality of Plasma-derived Products, 5 Blood Reviews 245 (1991), and U.S. Pat. Nos. 3,869,431, 5,110,907, 5,219,995, 7,531,513, and 8,772,461 which are herein incorporated by reference). One of skill in the art would recognize that adjustment of the above experimental parameters can be made in order to obtain specific protein fractions.

More recently, fractionation has reached further complexity, and as such, comprise additional embodiments of the invention. This recent increase in complexity has occurred through: the introduction of chromatography resulting in isolation of new proteins from existing fractions like cryoprecipitate, cryo-poor plasma, and Cohn fractions; increasing IgG recovery by integrating chromatography and the ethanol fractionation process; and viral inactivation/removal. (Id.) In order to capture proteins at physiological pH and ionic strength, anion-exchange chromatography can be utilized. This preserves functional activity of proteins and/or protein fractions. Heparin and monoclonal antibodies are also used in affinity chromatography. One of ordinary skill in the art would recognize that the parameters described above may be adjusted in order to obtain specifically-desired protein fractions.

In an embodiment of the invention, the plasma fraction may comprise a plasma fraction containing a substantial concentration of albumin (e.g. Albuminar®, Albutein®, Buminate®, Flexbumin®, Plasmanate®, Plasbumin®).

In other instances, the blood may be fractionated, e.g., to remove leukocytes, erythrocytes, platelets, antibodies, etc., and the plasma-comprising fraction, i.e., the "plasma-comprising blood product," retained for use. For example, the whole blood may be fractionated by filtration, centrifugation, etc., after collection is complete. As another example, the whole blood may be fractionated as it is drawn from the donor, and nonplasma components returned to the blood stream of the donor. For example, fractionated blood comprising plasma may be harvested by apheresis. By "apheresis" it is meant an automated blood collection in which harvested blood is passed through a machine that separates out certain components, e.g., leukocytes, red blood cells, plasma, etc., and returns the remaining blood components to the blood stream of the donor. In some instances, the apheresis is plasmapheresis, i.e., apheresis in which plasma is separated out and the remaining blood components returned to the donor's blood stream. In some such instances, the plasma-comprising blood product consists essentially of plasma.

In some embodiments, the plasma-comprising blood product, i.e., whole blood or plasma-comprising fraction thereof, is further processed to remove one or more polypeptide fractions, such as a polypeptide fraction having an average molecular below a predetermined threshold. While the predetermined threshold may vary, thresholds of interest include, but are not limited to: 3.5 kDa, 10 kDa, 25 kDa, 50 kDa. In some instances, a specific proteinaceous component may also be removed, e.g., IgG, etc. By the "average molecular weight" it is meant the mass of a polypeptide as calculated by multiplying the total number of amino acids in the polypeptide by the average molecular weight of 110 kD for each. A number of methods are known in the art for the removal of polypeptides that are a given molecular weight or less from liquid samples. For example, the blood product may be subject to size-exclusion chromatography (SEC), e.g., gel filtration chromatography, in which the plasma-comprising blood product is passed over a matrix of beads comprising pores that retard proteins of a given molecular weight or less, thereby depleting the flow-through of these small polypeptides. As another example, the blood product may be subjected to hydrodynamic chromatography (HOC), in which the parabolic or Poiseuille-like flow of a sample that develops under laminar flow through a tube or packed column causes larger particles to travel in the faster-moving flow at the center of the tube and smaller particles to be retarded along the slower-moving flow closer to the walls of the tube. Any convenient method, e.g., SEC, HOC, and the like, may be employed to remove proteins that have a given threshold average molecular weight or less from the blood product. Specific fractions of interest that may be employed in given embodiments of the invention include, but are not limited to: fractions in which polypeptides having an average molecular weight of 3.5 kDa or less have been removed; fractions in which polypeptides having an average molecular weight of 10 kDa or less have been removed; fractions in which polypeptides having an average molecular weight of 25 kDa or less have been removed; fractions in which polypeptides having an average molecular weight of 50 kDa or less have been removed; and fractions in which polypeptides having an average molecular weight of any of the above thresholds (e.g., 3.5 kDa, 10 kDa, 25 kDa, 50 kDa) or less and IgG has been removed. In other words, the blood product may be viewed a given molecular weight (e.g., 3.5 kD-; 10 kD; 25 kD-; 50 kD-) depleted plasma-comprising blood product. In some instances, the fraction that is administered is not a denatured fraction.

Plasma-comprising blood product, e.g., whole blood or a plasma-comprising fraction thereof, so prepared may then be administered to the individual suffering from or at risk of developing an aging-associated condition, e.g., cognitive impairment. In some embodiments, the plasma-comprising blood product is administered immediately, e.g., within about 12-48 hours of collection, to the individual suffering from or at risk of developing an aging-associated cognitive impairment. In such instances, the blood product may be stored under refrigeration, e.g., 0-10° C. In other embodiments, the plasma-comprising blood product is preserved, e.g., by cryopreservation, etc., as known in the art until such time as when it is to be administered to a recipient.

For example, a preparation may be frozen e.g., within about 24 or 48 hours of donation, i.e., immediately after collection to about 48 hours after collection and stored at about −20° C. or less, e.g., −80° C. or less, in some instances −90° C. or less, or −135° C. or less, e.g., −196° C. In some instances, the blood preparation is fresh-frozen, e.g., it is Fresh Frozen Plasma (FFP). In other instances, a chemical preservative, e.g., a cryopreservative, e.g., dimethyl sulfoxide (DMSO), may be added to aid in preservation. See, for example, Kreher et al. (2003) Journal of Immunological Methods 278:79-93; Reimann, et al. (2000) Clin. Diagn. Lab. Immunol. 7:352-359; and Romeu et al. (1992) J. Immunol. Methods 154:7-10. Cryopreservatives find particular use in maintaining the viability of cells in the blood product, for example, if the plasma-comprising blood product also comprises leukocytes, erythrocytes, etc. For example, 20% or more of the cells will survive upon thaw, for example, 40% or more, 60% or more, 80% or more cells, in some instances, 90% or more, such as 95% or more, 97% or more, or 99% or more of the cells will be viable after removal of the preservative. The blood product may be preserved prior to or after removal of proteins that are below a given threshold, such as described above, e.g., having an average molecular weight of 3.5 kD, 10 kD, 25 kD, 50 kD or less. In some instances, the blood product will be preserved prior to the depletion. In other instances, the blood product will be preserved after depletion. Following such techniques or techniques in the art, blood product may be stored for a year or more, e.g., 2, 3, 4, or 5 years or more, in some instances, 10, 20, 30 or 40 years or more, for example, 50, 60, 70 or 80 years. Upon thawing the blood product, the preservative, if used, may be replaced with any convenient solution, e.g., any suitable isotonic solution, in preparation for administration to the individual.

The plasma-comprising blood product may be administered using any convenient protocol for administering blood product to an individual. In some instances, the blood product is administered intravenously. The blood product may be mixed with intravenous solutions as known in the art, e.g., 5% dextrose in water, an isotonic electrolyte solution such as isotonic saline (0.9%), etc. The blood product may be administered using any convenient access device, e.g., needle for intravenous injection, compressor gun, peripheral cannula, central IV line, etc., e.g., implantable port, tunneled line, central venous lines, peripherally inserted central catheters and the like. Administration may be through any vein typically used for transfusion, e.g., subclavian, internal jugular, femoral, superior vena cava, inferior vena cava, right atrium, etc., in a volume and at a rate typically used for transfusion as known in the art, e.g., 10-20 ml per Kg weight of the individual per dose, at a rate of about 5 ml per minute.

In practicing the subject methods, the individual suffering from or at risk of suffering from an aging-associated condition, e.g., cognitive impairment or age-related dementia, is administered an effective amount of the young plasma product to treat the aging-associated condition, e.g., aging-associate cognitive impairment. In a clinical sense, an effective amount, or dose, of blood product is an amount of young plasma product that, when administered for a suitable period of time, usually at least about one week, and maybe about two weeks, or more, up to a period of about 3 weeks, 4 weeks, 8 weeks, or longer will evidence a reduction in the cognition decline and/or cognitive improvement in an individual suffering from impaired cognition or other type of degenerative condition due to natural aging or an aging associated disorder. For example, an effective dose is the dose that, when administered for a suitable period of time, such as at least about one week, and maybe about two weeks, or more, up to a period of about 3 weeks, 4 weeks, 8 weeks, or longer, will slow e.g., by about 20% or more, e.g., by 30% or more, by 40% or more, or by 50% or more, in some instances by 60% or more, by 70% or more, by 80% or more, or by 90% or more, e.g., will halt, cognitive decline in a patient suffering from natural aging or an aging-associated disorder. In some instances, an effective amount or dose of blood product will not only slow or halt the progression of the disease condition but will also induce the reversal of the condition, i.e., will cause an improvement in cognitive ability. For example, in some instances, an effective amount is the amount that when administered for a suitable period of time, usually at least about one week, and maybe about two weeks, or more, up to a period of about 3 weeks, 4 weeks, 8 weeks, or longer will improve the cognitive abilities of an individual suffering from an aging-associated cognitive impairment by, for example 1.5-fold, 2-fold, 3-fold, 4-fold, 5-fold, in some instances 6-fold, 7-fold, 8-fold, 9-fold, or 10-fold or more relative to cognition prior to administration of the blood product.

Cognition tests and IQ test for measuring cognitive ability, e.g., attention and concentration, the ability to learn complex tasks and concepts, memory, information processing, visuospatial function, the ability to produce and understanding language, the ability to solve problems and make decisions, and the ability to perform executive functions, are well known in the art, any of which may be used to measure the cognitive ability of the individual before and/or during and after treatment with the subject blood product, e.g., to confirm that an effective amount has been administered. These include, for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, the Alzheimer's Disease Assessment Scale (ADAS-Cog), the Psychogeriatric Assessment Scale (PAS) and the like. Progression of functional brain improvements may be detected by brain imaging techniques, such as Magnetic Resonance Imaging (MRI) or Positron Emission Tomography (PET) and the like. A wide range of additional functional assessments may be applied to monitor activities of daily living, executive functions, mobility, etc. In some embodiments, the method comprises the step of measuring cognitive ability, and detecting a decreased rate of cognitive decline, a stabilization of cognitive ability, and/or an increase in cognitive ability after administration of the blood product as compared to the cognitive ability of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

Biochemically speaking, by an "effective amount" or "effective dose" of blood product to prevent or treat an aging-associated cognitive impairment it is meant an amount of blood product that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, the reduction in synaptic plasticity and loss of synapses that occurs during the natural aging process or during the progression of an aging-associated disorder. In other words, cells contacted with an effective amount of blood product will become more responsive to cues, e.g., activity cues, which promote the formation and maintenance of synapses.

Improvements in synaptic plasticity may be observed both in vitro and in vivo as an induction of long term potentiation. For example, the induction of LTP in neural circuits may be observed in awake individuals, e.g., by performing non-invasive stimulation techniques on awake individuals to induce LTP-like long-lasting changes in localized neural activity (Cooke S F, Bliss TV (2006) Plasticity in the human central nervous system. Brain. 129(Pt 7):1659-73); mapping plasticity and increased neural circuit activity in individuals, e.g., by using positron emission tomography, functional magnetic resonance imaging, and/or transcranial magnetic stimulation (Cramer and Bastings (2000) Mapping clinically relevant plasticity after stroke. Neuropharmacology. 39(5): 842-51); and by detecting neural plasticity following learning, i.e., improvements in memory, e.g., by assaying retrieval-related brain activity (Buchmann A, et al. (2008) Prion protein M129V polymorphism affects retrievalrelated brain activity. Neuropsychologia. 46(9):2389-402) or, e.g., by imaging brain tissue by functional magnetic resonance imaging (fMRI) following repetition priming with familiar and unfamiliar objects (Soldan A, et al. (2008) Global familiarity of visual stimuli affects repetition-related neural plasticity but not repetition priming. Neuroimage. 39(1):515-26; Soldan A, et al. (2008) Aging does not affect brain patterns of repetition effects associated with perceptual priming of novel objects. J Cogn Neurosci. 20(10):1762-76). In some embodiments, the method includes the step of measuring synaptic plasticity, and detecting a decreased rate of loss of synaptic plasticity, a stabilization of synaptic plasticity, and/or an increase in synaptic plasticity after administration of the blood product as compared to the synaptic plasticity of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

The calculation of the effective amount of blood product to be administered may vary. The final amount to be administered will be dependent upon the blood product administered, the route of administration, and the nature of the disorder or condition that is to be treated. In some instances, the blood product will be administered once. In other instances, the blood product will be administered more than once, e.g., regularly, e.g., weekly, monthly, biannually, or annually. For example, the blood product may be administered weekly for 2 weeks or more, e.g., 3 weeks, 4 weeks, 5 weeks, 6 weeks, 7 weeks, 8 weeks, more than 8 weeks, etc. As another example, the blood product may be administered monthly, e.g., for 2 months or more, e.g., 3 months, 4 months, 5 months, 6 months, 7 months, 8 months, 9 months, 10 months, 11 months, 12 months, or more than 12 months. As another example, the blood product may be administered biannually, or annually. It will be understood by those of skill in the art that an initial dose may be administered for such periods of time, followed by maintenance doses, which, in some cases, will be at a reduced dosage.

In some embodiments, the subject blood product may be provided in conjunction with an active agent having activity suitable to treat aging-associated cognitive impairment. For example, a number of active agents have been shown to have some efficacy in treating the cognitive symptoms of Alzheimer's disease (e.g., memory loss, confusion, and problems with thinking and reasoning), e.g., cholinesterase inhibitors (e.g., Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g., citalopram (Celexa), fluoxetine (Prozac), paroxetine (Paxil), sertraline (Zoloft), trazodone (Desyrel), lorazepam (Ativan), oxazepam (Serax), aripiprazole (Ability), clozapine (Clozaril), haloperidol (Haldol), olanzapine (Zyprexa), quetiapine (Seroquel), risperidone (Risperdal), and ziprasidone (Geodon). In some embodiments, the subject blood product is provided before the second agent. In some embodiments, the subject blood product is provided after the second agent. In some embodiments, the subject blood product is provided concurrently with the second agent. In certain such embodiments, the subject blood product comprises one or more of these additional agents.

In some aspects of the subject methods, the method further comprises the step of measuring cognition and/or synaptic plasticity after treatment, e.g., using the methods described herein or known in the art, and determining that the rate of cognitive decline or loss of synaptic plasticity have been reduced and/or that cognitive ability or synaptic plasticity have improved in the individual. In some such instances, the determination is made by comparing the results of the cognition or synaptic plasticity test to the results of the test performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having a cognitive impairment, e.g., using the methods described herein or known in the art for measuring cognition and synaptic plasticity, prior to administering the subject plasma comprising blood product. In some instances, the diagnosing will comprise measuring cognition and/or synaptic plasticity and comparing the results of the cognition or synaptic plasticity test to one or more references, e.g., a positive control and/or a negative control. For example, the reference may be the results of the test performed by one or more age-matched individuals that experience aging-associated cognitive impairments (i.e., positive controls) or that do not experience aging-associated cognitive impairments (i.e., negative controls). As another example, the reference may be the results of the test performed by the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further comprise diagnosing an individual as having an aging-associated disorder, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy, dementia, and the like. Methods for diagnosing such aging-associated disorders are well-known in the art, any of which may be used by the ordinarily skilled artisan in diagnosing the individual. In some embodiments, the subject methods further comprise both diagnosing an individual as having an aging-associated disorder and as having a cognitive impairment.

As summarized above, aspects of the invention further include treating a subject for aging-associated conditions that are not aging-associated cognitive impairment conditions. For example, aspects of the invention include administration of young plasma products for the treatment of aging associated decline in peripheral organ function. As demonstrated in the experimental section below, rejuvenating and regenerative effects of young blood products were observed in muscle, liver, brain, heart, and pancreas. In some embodiments, the peripheral organ that benefits from administration with young plasma will include, but not be limited to, muscle, liver, brain, heart, pancreas, as well as other peripheral organs. In some embodiments the organ that will benefit from systemic administration of plasma will be the recipient's blood. Specifically, intercellular communication factors, which change with age, will be restored to more youthful levels; e.g., inflammatory factors, which increase with age will be reduced, while trophic factors, which decrease with age, will be increased.

In some instances, the methods result in a change in expression levels of one or moregenes in one or more tissues of the host, e.g., as compared to a suitable control (such as described in the Experimental section, below). The change in expression level a given gene may be 0.5 fold or greater, such as 1.0 fold or greater, including 1.5 fold or greater. The tissue may vary, and in some instances is nervous system tissue, e.g., central nervous system tissue, including brain tissue, e.g., hippocampal tissue. In some instances, the one or more genes whose expression is modulated, e.g., enhanced, is a gene encoding a product that is a member of a plasticity related signaling pathway (i.e., a synaptic plasticity regulation gene), e.g., Tlr4, Gria1, Kcnj10, Kdr, Ncam, Sdfr1, Egr1, Fos proteins, e.g., c-Fos, Drd1 a, Stxbp1, Mef2c, Cntn2, Junb, Bdnf and CamK2a, etc. In some instances, the modulation of hippocampal gene expression is manifested as enhanced hippocampal plasticity, e.g., as compared to a suitable control. In some instances, the one or more genes whose expression is modulated, e.g., enhanced, is a gene encoding a product that is a member of network related to synaptic plasticity and learning and memory, such as but not limited to: RELN, NTRK3, EPHA4, etc.

In some instances, treatment results in an enhancement in the levels of one or more proteins in one or more tissues of the host, e.g., as compared to a suitable control (such as described in the Experimental section, below). The change in protein level of a given protein may be 0.5 fold or greater, such as 1.0 fold or greater, including 1.5 fold or greater, where in some instances the level may approach that of a healthy wild-type level, e.g., within 50% or less, such as 25% or less, including 10% or less, e.g., 5% or less of the healthy wild-type level. The tissue may vary, and in some instances is nervous system tissue, e.g., central nervous system tissue, including brain tissue, e.g., hippocampal tissue. Target proteins of interest include, but are not limited to, synaptic proteins, e.g., synaptophysin, calcium binding proteins, e.g., calbindin.

In some instances, the methods result in one or more structural changes in one or more tissues. The tissue may vary, and in some instances is nervous system tissue, e.g., central nervous system tissue, including brain tissue, e.g., hippocampal tissue. Structure changes of interest include an increase in dendritic spine density of mature neurons in the dentate gyrus (DG) of the hippocampus, e.g., as compared to a suitable control. In some instances, the modulation of hippocampal structure is manifested as enhanced synapse formation, e.g., as compared to a suitable control. In some instances, the methods may result in an enhancement of long term potentiation, e.g., as compared to a suitable control.

In some instances, the methods result in enhancement in learning and memory, e.g., as compared to a suitable control. Enhancement in learning and memory may be evaluated in a number of different ways, e.g., the contextual fear conditioning and/or radial arm water maze (RAWM) paradigms described in the experimental section, below. When measured by contextual fear conditioning, treatment results in some instances in increased freezing in contextual, but not cued, memory testing. When measured by RAWM, treatment results in some instances in enhanced learning and memory for platform location during the testing phase of the task. In some instances, treatment is manifested as enhanced cognitive improvement in hippocampal-dependent learning and memory, e.g., as compared to a suitable control.

In some instances, treatment in accordance with methods described herein results in organism wide changes in intercellular communication proteins in blood, where the resultant protein changes may have pleiotropic beneficial effects on multiple tissues. Proteins of interest whose levels may be beneficially enhanced following treatment include, but are not limited to: growth factors, including IL-22, LIF, etc.

Aspects of the invention further include methods of screening candidate compositions, such as blood products comprising plasma, for activity with respect to treatment of aging associated conditions, e.g., for use in methods of the invention. Embodiments of methods include administering a candidate composition to a suitable animal model, and evaluating the animal model following administration to assess whether the candidate composition has a desired activity. Animal models of interest include non-human mammalian models, e.g., murine models that are able to tolerate human blood products, e.g., plasma, without experiencing harmful effects of immune rejection. Such animals include murine models that lack a functional immune system, such as NOD/SCID or "non-obese/diabetic/severe combined immunodeficiency" (NOD.CB17-Prkd$^{scid}$/Ncr-Crl, Strain Code 394, Charles River, Mass.) and NOD/SCID gamma (NSG) mice (Shultz et al. Human lymphoid and myeloid cell development in NOD/LtSz-scid IL2R gamma null mice engrafted with mobilized human hemopoietic stem cells. J Immunol 174, 6477-6489 (2005)) Additional murine models include: Athymic Nude (NU(Ncr)-Foxn1$^{nu}$), BALB/c Nude (CAnN.Cg-Foxn1$^{nu}$), CD-1® Nude (CD1-Foxn1$^{nu}$), Fox Chase SCID® Beige (CB17.CG-Prkdc$^{scid}$-Lyst$^{bg}$/), Fox Chase SCID® (CB17/Icr-Prkdc$^{scid}$/IcrIco), NIH-III nude (NIH-Lystb$^g$Foxn1$^{nu}$Btk$^{xid}$), NMRI nude, Nu/Nu Nude (NU-Foxn1$^{nu}$), OT I, OT II, SCH, SHO®, and SCID NCr, as well as the rat NR Nude (NIH-Foxn1$^{rnu}$) strain. The candidate composition may be any composition, such as but not limited to the blood products or fractions thereof described above. The animals may be assessed in a number of different ways, including at the gene expression level, protein level, structural level and behavioral level, e.g., using any of the assays and protocols described herein.

Utility

The subject methods and young plasma-comprising blood products find use in treating, including preventing, aging-associated conditions, such as impairments in the cognitive ability of individuals. Individuals suffering from or at risk of developing an aging-associated cognitive impairment that will benefit from treatment with the subject plasma-comprising blood product, e.g., by the methods disclosed herein, include individuals that are about 50 years old or older, e.g., 60 years old or older, 70 years old or older, 80 years old or older, 90 years old or older, and usually no older than 100 years old, i.e., between the ages of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments that are due to natural aging include the following:

Mild cognitive impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

Alzheimer's disease (ADJ. Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons>60 yr old, and its incidence increases as age advances. It accounts for more than 65% of the dementias in the elderly. The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Parkinson's Disease. Parkinson's Disease (PD) is an idiopathic, slowly progressive, degenerative CNS disorder characterized by slow and decreased movement, muscular rigidity, resting tremor, and postural instability. Originally considered primarily a motor disorder, PD is now recognized to also affect cognition, behavior, sleep, autonomic function, and sensory function. The most common cognitive impairments include an impairment in attention and concentration, working memory, executive function, producing language, and visuospatial function.

In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

Frontotemporal dementia. Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected: Behavioural variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies". Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

Huntington's disease. Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s). HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Amyotrophic lateral sclerosis. Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years. Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

Multiple Sclerosis. Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs. The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

Glaucoma. Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

Myotonic dystrophy. Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotoninprotein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

Dementia. Dementia describes class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall. Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (POD) would be the diagnosis when dementia onset is more than a year after the onset of Parkinson's. DLB is diagnosed when cognitive symptoms begin at the same time or within a year of Parkinson symptoms.

Progressive supranuclear palsy. Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as SteeleRichardson-Olszewski syndrome, reflecting the combined names of the scientists who defined the disorder. Although PSP gets progressively worse, no one dies from PSP itself.

Ataxia. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

Multiple-system atrophy. Multiple-system atrophy (MSA) is a degenerative neurological disorder. MSA is associated with the degeneration of nerve cells in specific areas of the brain. This cell degeneration causes problems with movement, balance, andother autonomic functions of the body such as bladder control or blood-pressure regulation. The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

In some embodiments, the subject methods and compositions find use in slowing the progression of aging-associated cognitive impairment. In other words, cognitive abilities in the individual will decline more slowly following treatment by the disclosed methods than prior to or in the absence of treatment by the disclosed methods. In some such instances, the subject methods of treatment include measuring the progression of cognitive decline after treatment, and determining that the progression of cognitive decline is reduced. In some such instances, the determination is made by comparing to a reference, e.g., the rate of cognitive decline in the individual prior to treatment, e.g., as determined by measuring cognition prior at two or more time points prior to administration of the subject blood product.

The subject methods and compositions also find use in stabilizing the cognitive abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive impairment in an individual suffering from an aging-associated cognitive impairment. In other words, cognitive ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-fold or more, following treatment by the subject methods relative to the cognitive ability that is observed in the individual prior to treatment by the subject methods. In some instances, treatment by the subject methods and compositions restores the cognitive ability in the individual suffering from aging-associated cognitive decline, e.g., to their level when the individual was about 40 years old or less. In other words, cognitive impairment is abrogated.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clontech.

Material and Reagents

USP saline was acquired from Hospira (Lake Forest, Ill.). Injections were performed with 27.5G or 30G needles, at a volume of 150 µL per injection. 18-year-old and >65-year-old plasma from human donors was collected by plasmapheresis by Biomat®, at multiple sites. Collection was performed under Biomat® standard operating procedures (SOPS) and retained 3 mL samples from the collections were provided. All materials were tested for absence of HIV, Hepatitis B and Hepatitis C. The vials were sent to the study site on dry ice.

Preparation

Upon arrival at the Study site, plasma samples from 45-50 donors from each age group were centrifuged at 3200 g at 0° C. for 30 minutes, filtered through a 0.22 µm filter, pooled for each age group, and aliquoted into 1 mL aliquots and frozen at −80° C. Vials were thawed for one hour on ice at the beginning of each day of injection, and in the event that an entire vial was not used, the vial was stored at 4° C. until the next injection day.

Animal Supply and Husbandry

The mouse strains NOD.CB17-Prkdcscid/NcrCrl ("NOD-scid", Strain Code 394, Charles River, Mass.) (Bosma, M. et al., The scid mouse mutant. 137 Curr Top Microbiol Immunol 197 (1988)) and NSG were used. Each mouse was ear punched to designate a unique identification number. All mice were individually housed under specific pathogen-free conditions under a 12-hour light, 12-hour dark cycle, and all animal handling and use was in accordance with IACUC approved standard guidelines.

Testing

Open Field

Open field tests were utilized to determine exploratory behavior of the subject mice. The open field test is an empty test arena, usually round or square. The mouse is placed inside a 50 cm×50 cm open filed arena for 10 minutes and the level of the mouse's activity is measured. Rearing time was measured by tracking the duration the forepaws were on the walls of the box. Total distance covered and velocity was also measured for duration of the test. CleverSys TopScan V3.0 (Reston, Va.) was used to track mouse behavior in open field. Open field chambers were constructed by CleverSys.

Y-Maze

Mice were allowed to explore two arms of a Y-maze (start+familiar) for 5 minutes. One hour later, mice were allowed to explore all three arms, and total time and number of entries in the arms were recorded.

Barnes Maze

Mice were trained on four consecutive days in the Barnes maze and given a maximum of 120 second to find the escape hole. The escape hole remained the same for four trials on a training day, but changed between training days. The latency to the escape hole was recorded for each mouse cohort on four separate training days.

DCX-Positive Cells

Doublecortin (DCX) is a microtubule-associated protein that is expressed by neuronal precursor cells. It is also expressed by immature neurons in embryonic and adult cortical structures. When they are actively dividing, neuronal precursor cells express DCX. The protein down-regulates after two weeks. Because of this association, it is useful as a marker of neurogenesis.

Brain tissue processing and immunohistochemistry was performed on free-floating sections well-described techniques (Luo, J. et al. Glia-dependent TGF-b signaling, acting independently of the TH17 pathway, is critical for initiation of murine autoimmune encephalomyelitis. J. Clin. Invest.

117, 3306-3315 (2007)). Mice were anesthetized and perfused with 0.9% saline. Brains were removed and subsequently fixed with phosphate-buffered 4% paraformaldehyde, pH 7.4, at 4° before sunk through 30% sucrose for cryoprotection. Brains were subsequently sectioned at 40 μm with a cryomicrotome. Sections were stored in cyroprotective medium. The primary antibody used was goat anti-Dcx (1:500, Santa Cruz Biotechnology). Primary antibody staining was revealed using biotinylated secondary antibodies and the ABCkit (Vector) with diaminobenzidine (DAB, Sigma-Aldrich) or fluorescence-conjugated secondary antibodies. In order to estimate the total number of Dcx-positive cells per dentate gyrus, immunopositive cells in the granule cell and subgranular cell layer of the dentate gyrus were counted in each sixth coronal hemibrain section through the hippocampus and multiplied by 12.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

The invention claimed is:

1. A method of testing a young human plasma fraction, the method comprising:
   a. administering the plasma fraction to an immunocompromised rodent, wherein the young blood plasma fraction has been prepared by a process comprising removing proteins having an average molecular weight below 25 kDa from plasma from a donor or donors 40 years old or younger, and
   b. measuring an effect of the plasma fraction on an endpoint, the endpoint being an indicator of hippocampal-mediated aging-associated cognitive impairment associated with a neurodegenerative condition.

2. The method of claim 1, wherein the endpoint comprises one or more of the following: neurogenesis, locomotor activity, anxiety, spatial memory, hippocampus dependent memory, and general cognition.

3. The method of claim 1, wherein the rodent is a mouse.

4. The method of claim 3, wherein the mouse is one of the following strains: NSG, athymic nude, BALB/c nude, CD-1® nude, Fox Chase SCID® Beige, Fox Chase SCID®, NIH-III nude, NMRI nude, NOD SCID, Nu/Nu Nude, OT I, OT II, SCH, SHO®, and SCID NCr.

5. The method of claim 1, wherein the rodent is a rat.

6. The method of claim 5, where in the rat is of the RNU nude strain.

7. The method of claim 1, wherein the plasma fraction lacks proteins having an average molecular weight of 10 kDa or less.

8. The method of claim 1, wherein the plasma fraction lacks proteins having an average molecular weight of 25 kDa or less.

9. The method of claim 1, wherein the plasma fraction is derived from a human younger than 5 years of age.

10. The method of claim 1, wherein the plasma fraction is derived from a human younger than 10 years of age.

11. The method of claim 1, wherein the plasma fraction is derived from a human younger than 15 years of age.

12. The method of claim 1, wherein the plasma fraction is derived from a human younger than 20 years of age.

13. The method of claim 1, wherein the plasma fraction is derived from a human younger than 25 years of age.

14. The method of claim 1, wherein the plasma fraction is derived from a human younger than 30 years of age.

15. The method of claim 1, wherein the plasma fraction is derived from a human younger than 35 years of age.

16. The method of claim 1, wherein the plasma fraction is derived from a human umbilical cord.

* * * * *